United States Patent [19]

Gervais et al.

[11] Patent Number: 4,535,621
[45] Date of Patent: Aug. 20, 1985

[54] PROCESS AND APPARATUS FOR MEASURING RHEOLOGICAL PROPERTIES OF SEMI-SOLID BODIES BY HARMONIC SHEAR IN ROTATION

[75] Inventors: Alain Gervais, Igny; Daniel Vermeire, Jouy en Josas; Olivier Cerf, Paris; Jacques Toux, Chartres, all of France

[73] Assignee: Institut National de la Recherche Agronomique, France

[21] Appl. No.: 545,300

[22] Filed: Oct. 25, 1983

[30] Foreign Application Priority Data

Oct. 25, 1982 [FR] France .................. 82 17835

[51] Int. Cl.³ .................. G01N 11/14; G01N 33/04
[52] U.S. Cl. .................. 73/59; 73/843
[58] Field of Search .................. 73/59, 64.1, 169, 843

[56] References Cited

U.S. PATENT DOCUMENTS

| | | | |
|---|---|---|---|
| 3,169,395 | 2/1965 | Enoch et al. | 73/59 X |
| 3,400,595 | 9/1968 | Pfeiffer | 74/47 |
| 3,636,753 | 1/1972 | Thiele et al. | 73/59 |
| 3,714,815 | 2/1973 | Hartert | 73/59 X |
| 3,732,724 | 5/1973 | Heinz | 73/59 |
| 4,154,093 | 5/1979 | Smith et al. | 73/54 |

FOREIGN PATENT DOCUMENTS

| | | | |
|---|---|---|---|
| 45-26839 | 9/1970 | Japan | 73/59 |
| 2028516 | 3/1980 | United Kingdom | 73/59 |

OTHER PUBLICATIONS

Journal of Scientic Instruments, vol. 42, 1965, E. W. Billington, Coaxial Cylinder Viscometer for use Under Oscillatory and Transient Conditions.

*Primary Examiner*—Stewart J. Levy
*Assistant Examiner*—Joseph W. Roskos
*Attorney, Agent, or Firm*—Jones, Tullar & Cooper

[57] ABSTRACT

A process and apparatus for measuring rheological properties of semi-solid bodies. The apparatus comprises a vessel (4) containing the body (5) to be tested, a measuring head (3) immersed in the vessel (4) in the middle of the body, and a drive for driving the head (3) in rotation through the intermediacy of an axle. The driver imparts a sinusoidal or pseudo-sinusoidal rotational motion to the axle (2), a torque sensor (7) and an angle sensor (8) which are mounted on the axle (2) and are both connected to a processing device for processing information, such as a device for processing signals (9) connected to a microcomputer (10).

12 Claims, 10 Drawing Figures

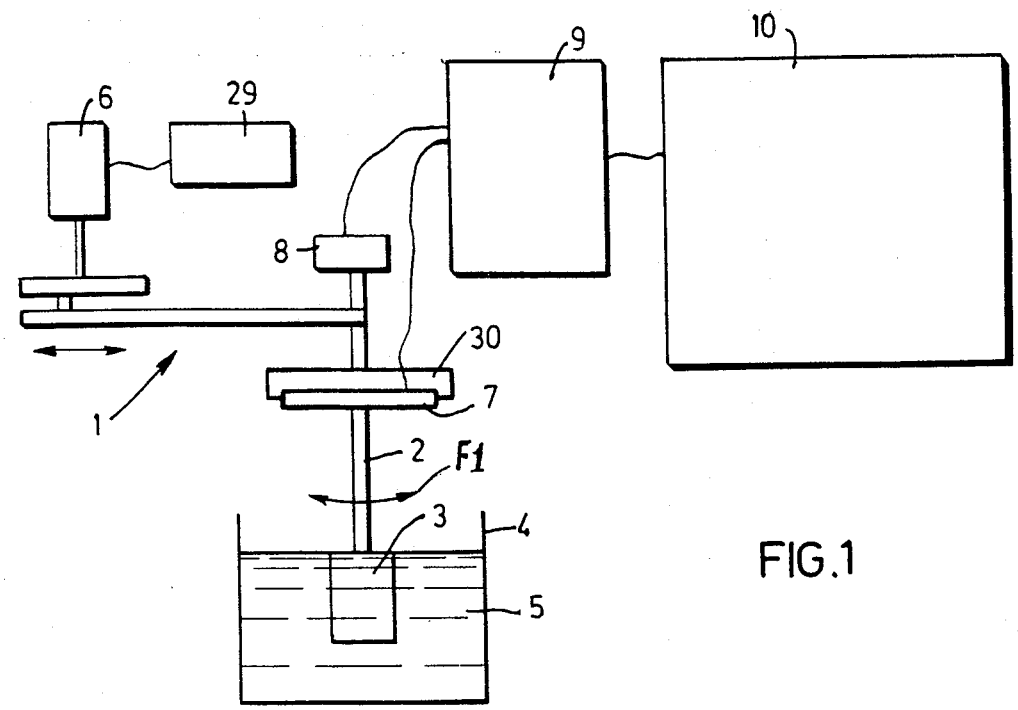
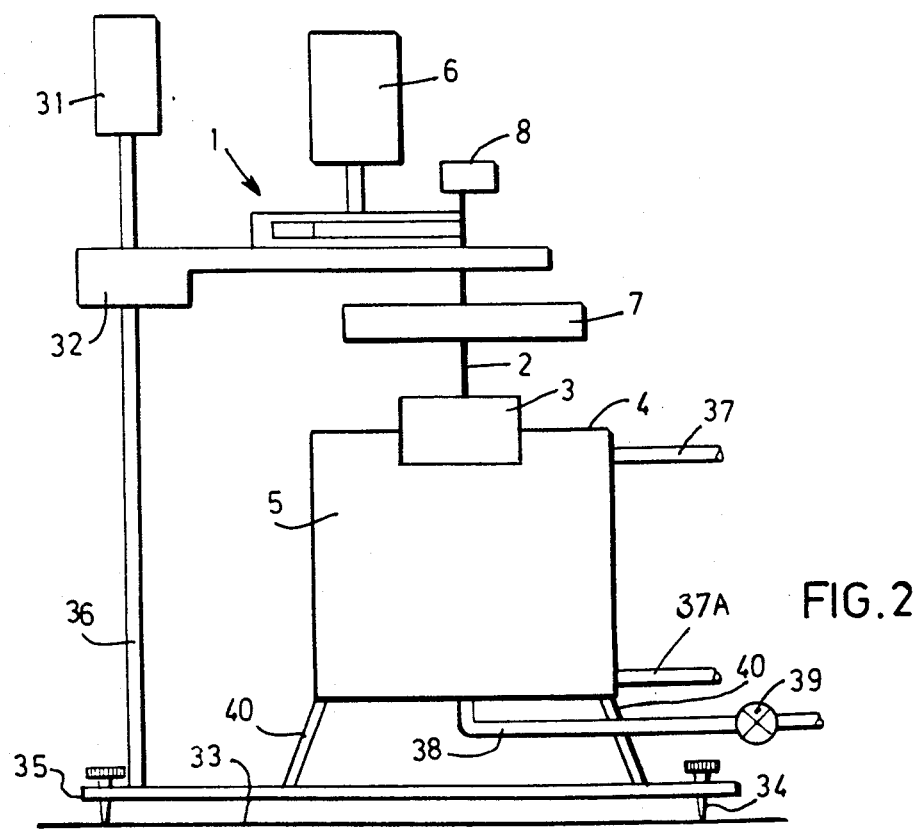
FIG.1
FIG.2

PROCESS AND APPARATUS FOR MEASURING RHEOLOGICAL PROPERTIES OF SEMI-SOLID BODIES BY HARMONIC SHEAR IN ROTATION

BACKGROUND OF THE INVENTION

1. Field of the Invention

The present invention relates to a process and an apparatus for measuring rheological properties of semi-solid bodies by harmonic shear in rotation. The said apparatus can be called a viscoelastometer.

The invention makes it possible to study both simple rheological properties (viscosity, elasticity) and complex rheological properties (viscoelasticity, plasticity, viscoplasticity, etc.) of numerous semi-solid bodies or substances.

The applications of the present invention are very numerous.

Examples of semi-solid products are represented by products in the form of gels and creams. There may be mentioned in particular the gels of gelatine, starch, milk, ice creams, marshmallow, jam, chocolate creams, honey, dairy cream and other food products, as well as coagulated blood and similar semi-solid substances.

The present invention also has an application in the plastics industry, rubber industry, wax industry and petroleum products industry.

The invention applies generally to all the semi-solid bodies. Nevertheless, it has a particular application in the cheese industry for choosing the time for cutting the coagulum or curd in cheese making.

The invention employs a harmonic rotational shear and makes it possible to measure the required physical quantities accurately in international system units.

Because of the low shear produced in the product, the structure of the product is not destroyed and it is possible to follow the change in its rheological properties with time.

The apparatus is completely automatic and can be employed in the laboratory as well as in control systems and in industrial manufacturing systems.

It is known that rheology is a field of technology concerned with the study of relationships between stresses and strains.

The subject of the present invention is a process for measurement and a measuring apparatus of a design which is, at the same time, simple, efficient and reliable and permits a deformation to be produced in a semi-solid product through the intermediacy of a measuring head oscillating around its vertical axis and driven with a sinusoidal of pseudo-sinusoidal rotational movement with controllable frequency and amplitude, the measurement of the torque produced in the product around the head being carried out by a torque sensor mounted on the axle or shaft.

So far as it is known, there is at the present time no known apparatus for measuring rheological properties of semi-solid bodies in which the axle carrying the measuring head is driven in a perfectly sinusoidal rotational movement.

2. Description of the Prior Art

In the prior art use is made of a special apparatus for milk, known under the name of Torsiometer, marketed by the Company Plint and Partners in which the amplitude and the frequency of oscillation of the cylinder are fixed. This apparatus is manual and its torque measuring system cannot provide international system units.

Such an apparatus can only work with a wide gap (the gap being the distance between the measuring head and the wall of the vessel) and its motion is not constant in the course of the gelling of the milk.

GENERAL DESCRIPTION OF THE INVENTION

The apparatus according to the invention is entirely automatic and can work either with a narrow gap or a wide gap.

According to a first subject, the invention relates to a process for measuring the rheological properties of semi-solid bodies consisting in introducing into the body a measuring head which can move in rotation and in determining the conditions of motion of the head, which serve as values representing the said rheological properties on account of stresses applied by the head moving within the body, wherein the measuring head is driven with a sinusoidal or pseudo-sinusoidal motion, with controllable frequency and amplitude, and independently of the body to be tested.

According to another subject, the invention relates to an apparatus for measuring rheological properties of semi-solid bodies comprising essentially a vessel containing the body to be tested, a measuring head immersed in the vessel, within the body, means for driving the said head in rotation through the intermediacy of an axle, and means for determining the rotational torque on the axle, wherein the said apparatus comprises for driving the axle with a sinusoidal or pseudo-sinusoidal rotational motion, a torque sensor and an angle sensor which are mounted on the axle and are both connected to means for processing information, such as a device for processing signals connected to a microcomputer.

The process and the apparatus for measurement according to the present invention make use of harmonic rotational shear within the semi-solid body to be measured.

The present invention also relates to the following features, considered in isolation or according to any of their technically feasible combinations:

the reciprocating rotational motion of the head axle is obtained starting from a continuous circular motion which is converted into rectilinear reciprocating motions and then into a sinusoidal or pseudo-sinusoidal rotational motion;

the means for driving the axle carrying the measuring head immersed in the semi-solid bodies to be tested with a sinusoidal rotational movement consist of a kinematic system comprising a disc driven by a motor, a bearing fixed to the disc and turning around an axis parallel to the axis of rotation of the disc, a stage against which the bearing rests by virtue of a spring, a carriage supported by the said stage, a rectilinear rack integral with the carriage and a toothed sector engaged with the said rack, the axle of this sector being the axle carrying the measuring head, the means for driving the axle with a sinusoidal rotational movement consist of another kinematic system comprising a table with a double rectilinear cross motion comprising two moving parts and a fixed part, means for driving the axle carrying the measuring head with a pseudo-sinusoidal motion, comprising two discs, a first disc driven in continuous rotation by the motor and equipped with an attachment point for a filament or ribbon which is hooked at a point of attachment on a second disc which comprises a tension spring, the said means consist of a torque motor and control electronics, the said means consist of a friction device, the torque sensor mounted on the axle is a hollow metallic part provided with a plurality of perforations and comprising at least two arms or weakened parts to which strain gauges are bonded, the said metallic part being capable of deformation in the region of the grounds, the strain gauges are resistance or capacitance strain gauges whose connection forms a bridge, particularly a Wheatstone bridge, so that each arm of the bridge encloses the series of gauges corresponding to the same place on the arms of the sensor, the amplitude of the measuring head driven with a sinusoidal or pseudo-sinusoidal rotational motion is in the range from 0° to ±90° particularly from 0° to ±20°, and the frequency range is between 1 millihertz and 10 hertz, particularly between 1 mHz and 1 Hz, the measuring head is in the shape of a cylinder, a cone or of a flat part.

BRIEF DESCRIPTION OF THE DRAWINGS

Other advantages and characteristics of the present invention will also become apparent from the detailed description given below with reference to the attached drawings, in which:

FIG. 1 is an outline diagram illustrating the invention.

FIG. 2 illustrates a concrete example of some components of FIG. 1.

DESCRIPTION OF THE PREFERRED EMBODIMENT

Figure 3:
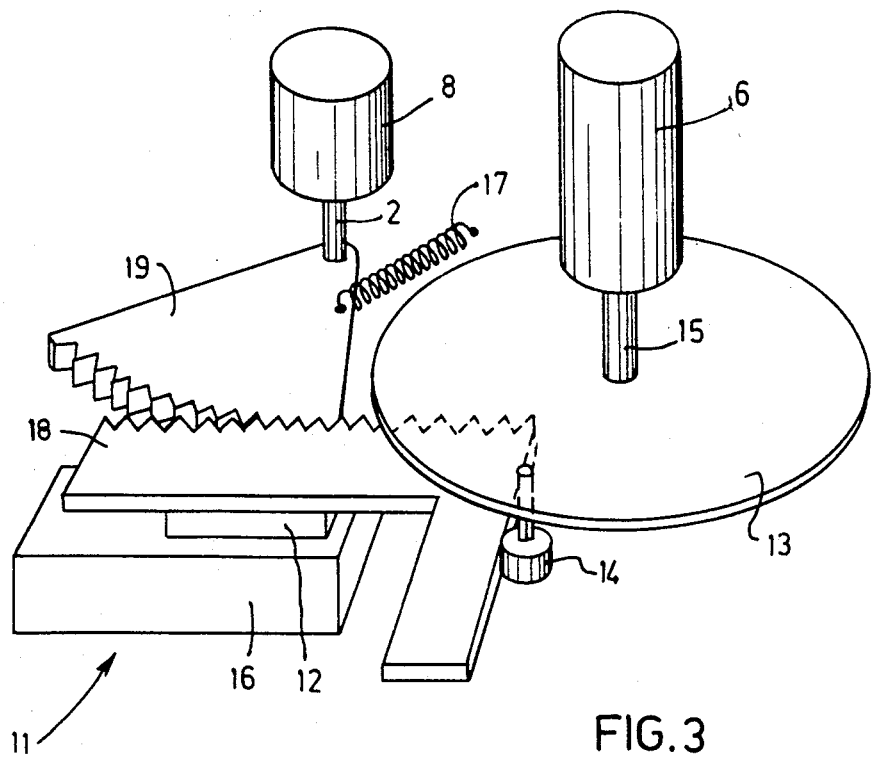
FIG. 3 is a view in perspective of the means for obtaining a sinusoidal rotational motion.

In the attached drawings, where the same reference symbols indicate analogous components, FIG. 1 is an outline diagram which illustrates the present invention.

Starting with a motor 6 controlled by electronics 29, a continuous circular motion is converted into a rectilinear reciprocating motion and then into a sinusoidal rotational motion of an axle 2, by means 1 described in greater detail hereafter. The axle 2 which is driven with such a movement according to the arrow $F_1$ in FIG. 1 carries at an end a measuring head 3 immersed in the semi-solid product 5 which is to be tested arranged in a vessel 4. The axle 2 also carries a torque sensor 7 and its fixing mounting as well as an angle sensor 8, both connected to a signal processing device 9, connected to a microcomputer 10. The motor 6 could, in fact, be controlled directly by the device 9.

The device 9 makes possible the electrical supply of the various components, processing and display of the signals, frequency control of the apparatus and transmission of the signals in an analog form or a digital form. It is therefore possible, starting with the device 9, to control the speed of rotation of the motor 6 through the intermediacy of a controllable stabilised voltage (servo motor) or of a controllable stabilised frequency base (stepping motor).

FIG. 2 shows an example of embodiment. The apparatus of the invention is arranged on a table 33. A support 35 which is adjustable for horizontal levelling rests on the table 33 and can be adjusted with the screws 34. A vertical column 36 carries a motor 31 for raising and lowering a stage 32 supporting the means 1 for transforming a continuous circular motion imparted by the motor 6. The torque sensor 7 and the angle sensor 8 are mounted on the axle 2, at one end of which the measuring head 3 is immersed in the vessel 4 filled with the semi-solid product 5 which is to be tested. The vessel 4 is a vessel which is thermostated by a liquid circulating in a jacket. The circulation of the liquid is shown diagrammatically at 37 and 37A. The vessel 4 rests on the adjustable support 35 by means of feet 40. A pipe 38 for draining the vessel 5 comprises a stop valve 39.

FIG. 3 illustrates an embodiment for obtaining a sinusoidal rotational motion.

In the example under consideration, the motor 6 imparts, through the intermediacy of the axle 15, a continuous circular motion to a disc 13. This continuous circular motion is first converted on the carriage 12, which is a component of the kinematic system 11, into a rectilinear sinusoidal motion. This conversion is carried out through the intermediacy of a bearing 14 which is fixed at an adjustable distance from the axis of rotation 15 of the motor 6 and which bears against a stage 16 having a rectilinear movement. The stage 16 supports the carriage 12. The required pressure of the bearing 14 against the stage 16 is ensured by a spring 17. In this embodiment the bearing 14 must always bear against the stage 16. The carriage 12 on which a rectilinear sinusoidal motion is produced carries a rack 18 which engages with a toothed sector or pinion 19 with automatic elimination of backlash. The rack 18-pinion 19 assembly converts the sinusoidal rectilinear motion into a rotational sinusoidal motion which is imparted to the axle 2 on which are arranged both the angle sensor 8 and the torque sensor 7 which is not shown in FIG. 3.

Figure 4:
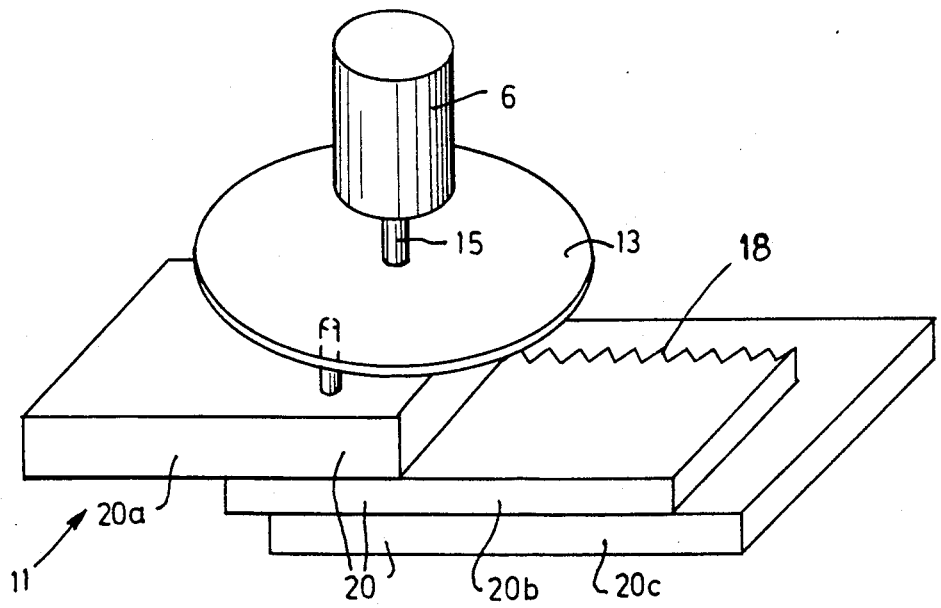
FIG. 4 is an alternative version of FIG. 3.

FIG. 4 shows another embodiment of the kinematic system 11.

Figure 5:
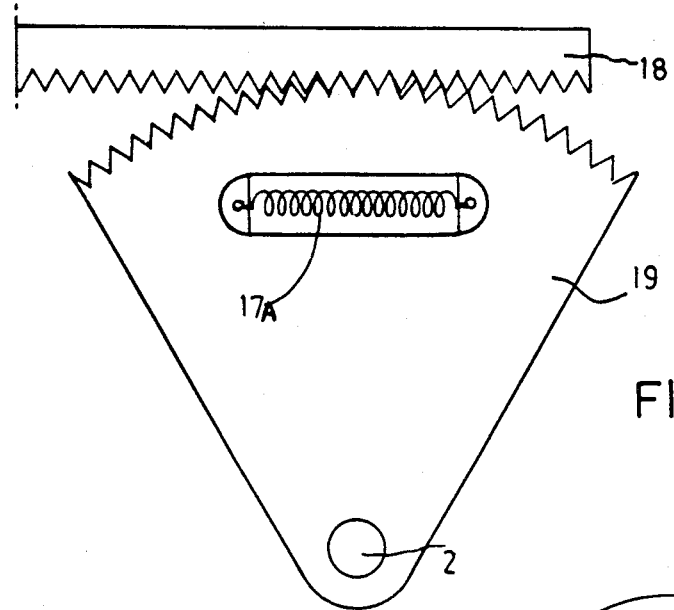
FIG. 5 illustrates a very simple example of conversion of a rectilinear reciprocating motion into sinusoidal rotational motion with the aid of two superposed toothed sectors driving a rectilinear rack and connected to each other by the spring, shown diagrammatically.
Figure 10:
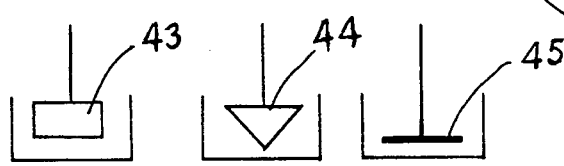
FIG. 10 shows three different types of measuring head.

In this alternative, provision is made, for the conversion of the motion imparted by the motor 6, for a table or stage 20 having a double rectilinear cross movement, comprising two movable parts 20a and 20b and a fixed part 20c. The movable part 20b carries the rack 18 and the motion is converted with the aid of the toothed sector 19 on the axle 2 as shown diagrammatically in FIG. 5.

This embodiment with the table 20 having a double rectilinear cross motion does not require the use of the spring 17 employed in the embodiment according to FIG. 3. In fact, in this embodiment there is no stage 16 to be united with the bearing 14. The conversion of the motion is carried out by the table or stage 20. In this embodiment, use is made of the system for converting the motion shown in FIG. 5. In this figure it is understood that only one of the two superposed toothed sectors is visible; nevertheless, it is possible to use an analogous system consisting of two racks connected together by a spring 17A and driving a single toothed sector 19.

Figure 6:
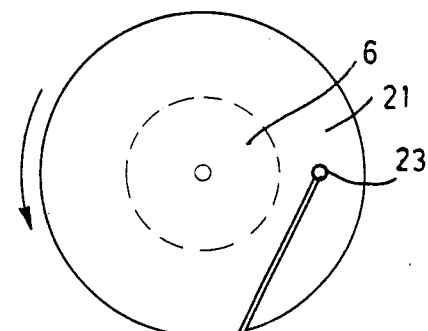
FIG. 6 shows a simplified version with which the motion obtained is a pseudo-sinusoidal motion.

FIG. 6 relates to an embodiment which is highly simplified and having an attractive cost of manufacture.

Starting from the motor 6 having the same characteristics as those mentioned above, a pseudo-sinusoidal rotational motion is produced. This conversion is obtained by means of two discs or wheels 21 and 22 connected by a filament or ribbon 24. The filament or ribbon 24 is hooked at a point of attachment 23 on the disc 21 which is driven with a continuous circular motion in the direction of the arrow with the aid of the motor 6.

The motion is converted by the filament or ribbon 24 hooked at the point 25 on the disc or wheel 22 which comprises a tension spring 17B.

It is readily understood that, if the length of the filament or ribbon 24 were infinite, a sinusoidal rotational movement would be obtained at the axle 2.

However, in reality the filament or ribbon 24 is not infinite and therefore in this case a pseudo-sinusoidal rotational motion is obtained. Nevertheless, this embodiment is highly advantageous for some determinations, on account of the simplicity of the embodiment.

As mentioned above, the means 1 for converting motion can be of a mechanical type—which is the case for the two kinematic systems 11 and the simplified version according to FIG. 6—or of an electronic type with a torque motor and control electronics.

Figure 7:
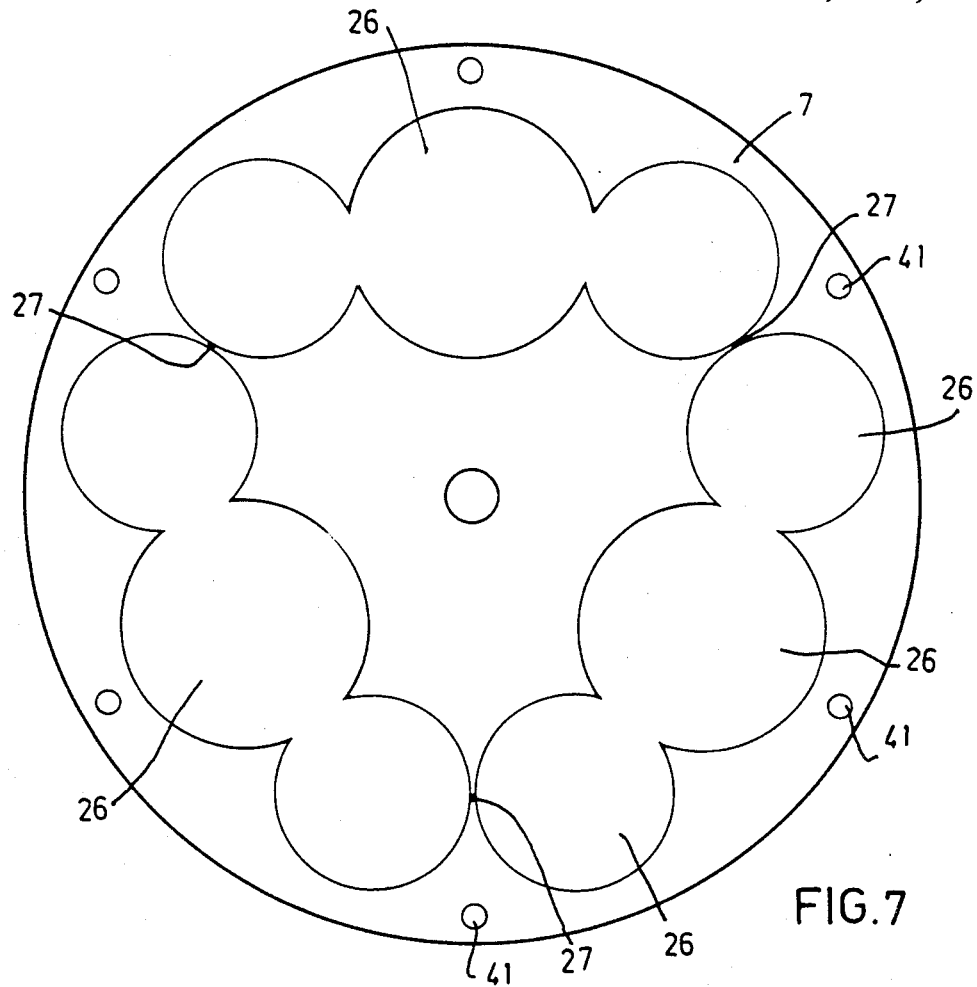
FIG. 7 shows a torque sensor.

FIG. 7 shows the torque sensor arranged on the axle 2. The flange (or mounting) 30 illustrated diagrammatically in FIG. 1 ensures the mounting of the said torque sensor 7.

Figure 8:
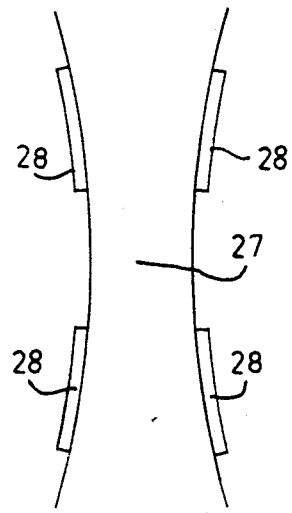
FIG. 8 is an enlarged view of an arm or ground on which strain gauges are bonded.

The torque sensor 7 is in the form of a piece of metal, preferably of circular shape, provided with a plurality of perforations 26 so as to form arms or weakened parts 27 reduced in thickness, for example down to a size of 0.1 mm. The arms or weakened parts 27 will serve for carrying out the required determinations. The torque sensor 7 comprises at least two arms or weakened parts 27. The weakened parts 27 are a consequence of the geometrical layout of the perforations 26. It is quite evident that it would be possible to operate by arranging the weakened parts 27 both on an inner part and an outer part of the sensor. The torque sensor is highly sensitive with respect to torque and is stiff in the other directions, namely in thrust or in traction. Three arms are shown in FIG. 7; naturally, this is by way of example and the number greater than two arms is not limiting. 41 refers to holes by means of which the torque sensor 7 is fastened, for example with the aid of screws, to the support mounting or flange 30. The torque sensor 7 is made of an alloy of a good metrological quality, more particularly in relation to its elastic linearity, its hysteresis and its recovery to zero. Bonded to each arm or weakened part 27 are strain gauges 28 which can be of a capacitance, resistance or other type. In the example shown in FIG. 8, four gauges 28 have been bonded to an arm 27. The connection of the gauges 28 is preferably formed into a bridge, particularly a Wheatstone bridge, so that each arm of the bridge contains the series of gauges corresponding to the same place on the arms of the sensor. In this manner the variabilities of thickness of the arms of the sensor are eliminated.

Figure 9:
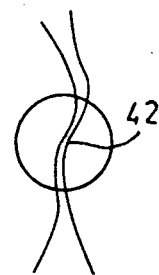
FIG. 9 shows the S-deformation obtained in the region of a ground.

FIG. 9 shows at 42 the S-deformation obtained during a measurement.

The conditioning of the bridge of gauges 28 is carried out by the device 9 which ensures a controllable stabilized supply.

As an example, a supply of up to 6 volts per arm 27 of sensor 7 can be provided for gauges having a resistance of 350 ohms.

The angle sensor 8 is a conventional sensor; as a result it will not be described further since those skilled in the art are well acquainted with such a device.

In addition to the functions described above, the device 9 permits equilibration of the bridge of gauges 28, signal amplification and filtering.

It also permits the stabilized supply of the angle sensor 8, the display of all the measured voltages and the display of stresses.

It comprises analog outputs corresponding to the measured voltages. It can receive a digital interface ensuring the control and the recovery of data from a calculator.

The measuring heads 3 can be of various shapes, consisting, for example, of a cylinder 43, a cone 44 or a flat part 45, or any other shape having a symmetry of rotation.

The apparatus according to the present invention permits non-destructive testing to be carried out. Furthermore it permits knowledge of the change in the rheological properties with time. A particularly useful application of this apparatus relates to the cheese manufacturing industry.

In cheese manufacture, the choice of the cutting of the cheese coagulum or curd is a critical stage in the manufacture of cheeses.

Until the present time use was made of empirical methods such as touch or the application of setting time multiplier factors.

The semi-empirical instrumental methods employ instruments such as penetrometers or devices for measuring the stiffness. None of these techniques is really satisfactory.

The apparatus according to the invention is of a universal nature permitting, according to the choice of the width of the gap, to carry out measurements of pure viscosity and pure elasticity. In the cheese making application, starting with the change of the measured rheological parameters, the computer 10 will choose the optimum moment for the cutting, the optimum control of the cutting of the coagulum, cutting of curd and of the mechanical work (stirring) of the curd in a vat.

It is clear that the apparatus of the invention can be used in many other applications, for example for the in-line control of products to determine the kinetics of gelling of various products.

The apparatus according to the invention, which is simple to produce on account of its structure, provides results which have never been obtainable until this time.

What is claimed is:

1. A process for measuring rheological properties of semi-solid bodies utilizing a measuring head (3) including an axle, comprising the steps of:
   introducing the measuring head into the body to be tested;
   reciprocally rotating the measuring head axle starting from a continuous circular motion, converting said continuous circular motion into a rectilinear reciprocating motion and then into a sinusoidal or pseudo-sinusoidal rotational motion, thereby driving the measuring head with a sinusoidal or pseudo-sinusoidal rotational motion, with controllable frequency and amplitude, and independently of the body to be tested; and determining the conditions of motion of the head which serve as values representing the rheological properties of the semi-solid body due to the stressed applied by the head moving within the body.

2. An apparatus for measuring rheological properties of semi-solid bodies comprising essentially a vessel (4) containing the body to be tested (5), a measuring head (3) immersed in the vessel (4), within the body, and means for driving the said head (3) in rotation through the intermediacy of an axle (2), which comprises means (1) for driving the axle (2) with a sinusoidal or pseudo-sinusoidal rotational motion, a torque sensor (7) and an angle sensor (8) which are mounted on the axle (2) and are both connected to means for processing information, such as a device for processing signals (9) connected to a microcomputer (10).

3. The apparatus as claimed in claim 2, wherein the means (1) for driving the axle (2) with a sinusoidal rotational movement form a kinematic system (11) comprising a disc (13) driven by a motor (6), a bearing (14), fixed to the disc (13) and turning around an axis parallel to the axis of rotation (15) of the disc (13), a stage (16) against which the bearing (14) rests by virtue of the spring (17), a carriage (12) supported by the said stage (16), a rectilinear rack (18) integral with the carriage (12) and a toothed sector (19) engaged with the said rack (18), the axle of this sector (19) being the axle (2) carrying the measuring head (3).

4. The apparatus as claimed in claim 2, wherein the means (1) for driving the axle (2) with a sinusoidal rotational motion consists of a kinematic system (11) comprising a table (20) with a double rectilinear cross motion, comprising two moving parts (20a) and (20b) and a fixed part (20c).

5. The apparatus as claimed in claim 2, wherein the means (1) for driving the axle (2) carrying the measuring head (3) with a pseudo-sinusoidal rotational motion comprise two discs (21, 22), the first disc (21) being driven in continuous rotation by the motor (6) and being equipped with an attachment point (23) for a filament or ribbon (24) which is hooked at a point of attachment (25) on the second disc (22), which comprises a spring (17B) intended to keep the filament or ribbon (24) tensioned.

6. The apparatus as claimed in claim 2, wherein the means (1) for driving the axle (2) carrying the measuring head (3) with a sinusoidal rotational motion consist of a torque motor and control electronics.

7. The apparatus as claimed in claim 2, wherein the means (1) for driving the axle (2) carrying the measuring head (3) with a sinusoidal rotational motion consist of a friction device.

8. The apparatus as claimed in any one of claims 2 to 7, wherein the torque sensor (7) fixed on the axle (2) is a hollow metallic part provided with a plurality of perforations (26) and comprising at least two arms or grounds (27) to which strain gauges (28) are bonded, the said metallic part being capable of deformation in the region of the weakened parts (27).

9. The apparatus as claimed in any one of claims 2 to 7, wherein the strain gauges (2) are resistance or capacitance strain gauges whose connection forms a bridge, particularly a Wheatstone bridge, so that each arm of the bridge encloses the series of gauges corresponding to the same place on the arms (27) of the sensor (7).

10. The apparatus as claimed in any one of claims 2 to 7, wherein the amplitude of the measuring head (3) driven with a sinusoidal or pseudo-sinusoidal rotational motion is in the range from 0 to ±90°, particularly from 0 to ±20° and the frequency range is between 1 millihertz and 10 hertz, particularly between 1 mHz and 1 Hz.

11. The apparatus as claimed in any one of claims 2 to 7, wherein the measuring head (3) is in the shape of a part having a symmetry of rotation such as, for example, a cylinder, a cone or a flat part.

12. The application of the process and of the apparatus as claimed in any one of claims 1 to 7 in the cheese manufacturing industry for the choice of the time of cutting the coagulum or the curd in cheese making.

* * * * *